Figure 1:
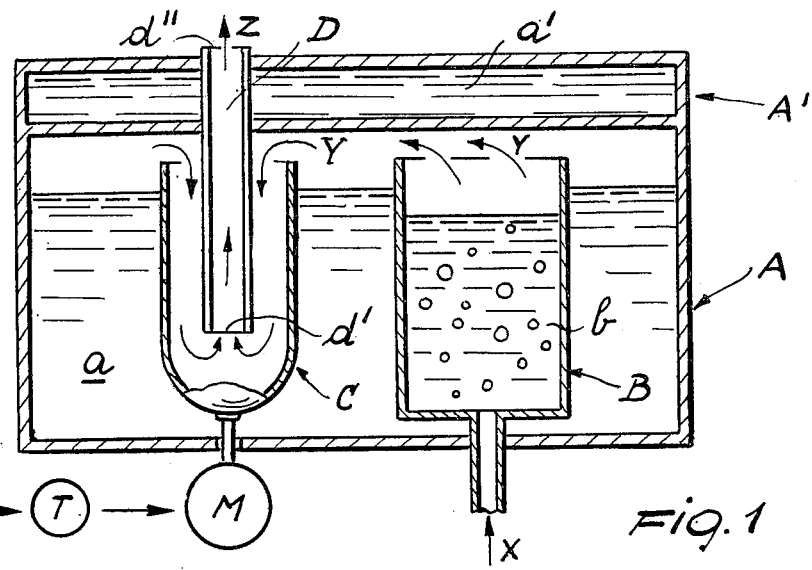

United States Patent [19]
Raffaele et al.

[11] 3,973,915
[45] Aug. 10, 1976

[54] BLOOD EQUILIBRATOR

[75] Inventors: Italo Raffaele; Luigi Rossi, both of Milan, Italy

[73] Assignee: Instrumentation Laboratory, Inc., Lexington, Mass.

[22] Filed: Aug. 14, 1974

[21] Appl. No.: 497,256

Related U.S. Application Data

[63] Continuation-in-part of Ser. No. 493,316, July 31, 1974, abandoned, which is a continuation of Ser. No. 240,961, April 4, 1972, abandoned.

[30] Foreign Application Priority Data

Apr. 9, 1971  Italy.................................. 22982/71

[52] U.S. Cl................................. 23/259; 23/230 B; 23/253 R; 23/258.5 R; 55/68
[51] Int. Cl.².................. B01L 11/00; G01N 31/00; G01N 33/16
[58] Field of Search.............. 23/259, 230 B, 253 R, 23/258.5; 55/68

[56] References Cited
UNITED STATES PATENTS

| | | | |
|---|---|---|---|
| 2,693,802 | 11/1954 | Osborn | 23/258.5 |
| 2,702,035 | 2/1955 | Gibbon et al. | 23/258.5 |
| 3,127,254 | 3/1964 | Astrup et al. | 23/253 R X |

FOREIGN PATENTS OR APPLICATIONS

| | | | |
|---|---|---|---|
| 1,123,494 | 2/1962 | Germany | 23/230 B |

*Primary Examiner*—Barry S. Richman

[57] ABSTRACT

Equilibrator device for use in determination of the acid-base status, the oxygen dissociation curve of blood and other properties of physiological interest. The device comprises, within a confined and thermostatically controlled environment, a cuvette for accommodating a sample of blood or other liquid to be equilibrated with a gas phase, means for controlledly rotating such cuvette and means for promoting passage of a gaseous flow firstly through a humidifying ambient and then into the presence of said sample.

18 Claims, 3 Drawing Figures

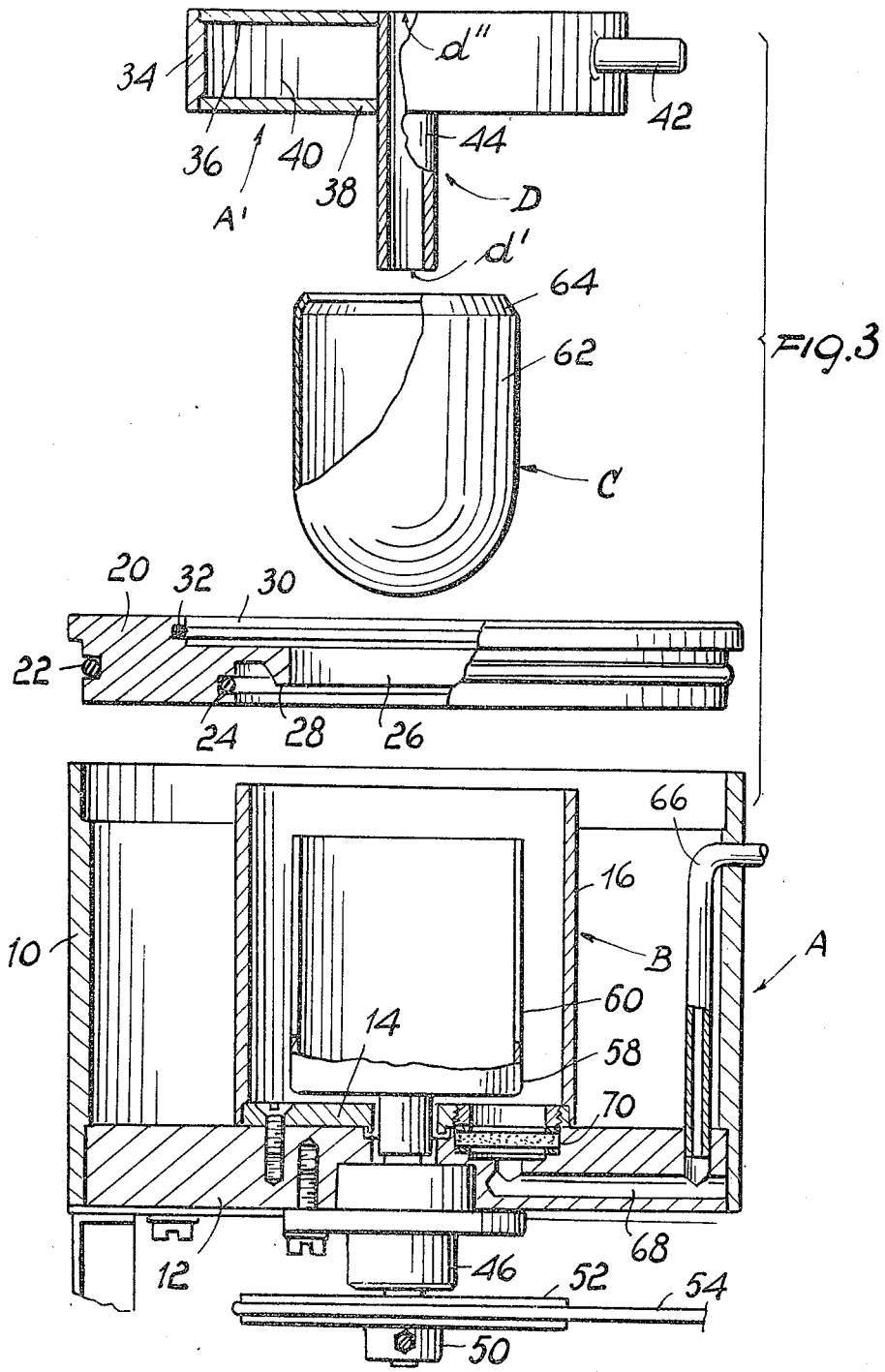

BLOOD EQUILIBRATOR

This application is a continuation-in-part of our application Ser. No. 493,316, filed July 31, 1974 and now abandoned, which is a continuation of Ser. No. 240,961, filed Apr. 4, 1972, entitled "BLOOD EQUILIBRATOR" and now abandoned.

SUMMARY OF INVENTION

This invention is concerned with devices for studying certain physiological and physico-chemical properties of blood and possibly of other organic liquids and more particularly it is concerned with devices, usually termed "equilibrators" used in the determination of the acid-base status and oxygen dissociation curve (ODC) of blood, by equilibrating a blood sample with a chosen value of oxygen pressure, carbon dioxide pressure and base excess. Still more particularly the invention is concerned with a new and improved device for the equilibration of blood with a gas phase of suitable $O_2$ and $CO_2$ content by applying the "open" method or system.

The art of studying the above outlined properties of blood is known as well as equilibrating a blood sample with a gas phase of suitable content. This art pertains to physiology and physiological chemistry and further comments thereabout are unnecessary for further understanding of the invention. As a general indication, it will be of interest to recall that such equilibration can and has usually been carried out by either of two methods, that is (i) the "closed" method and (ii) the "open" method. The closed method has been extensively made use of in the past, in particular by applying the teachings of the Van Slyke and Henderson Schools. The closed method comprises equilibrating, in a glass tonometer, a sample of blood and then individually analyzing its gaseous and its liquid phases. Such a method is difficult and time consuming and it has been proved to be not as suitable as is desirable for routine work.

More recently the procedure for equilibrating samples of blood by the open method has been developed. According to this latter procedure a suitable gas or gaseous mixture is caused to continuously flow over the blood sample until equilibrium is reached. Equilibrators adapted for operating according to the open method, such as the Astrup microequilibrators, have become commercially available.

It is therefore an object of this invention to provide a new and advantageous equilibrator designed for operating according to the open method and sharply improving the art and the technology of such equilibration both as to the time required to attain the desired measurements and as to the time and manner by which measurements of the desired precision can be attained. More particularly, specific objects of this invention comprise providing a new and improved equilibrator wherein variable volumes of blood, such as from 1 to 8.0 cc. of blood can be accommodated and processed wherein, for example an easily and promptly removable and replaceable vessel for the blood sample is provided, wherein the blood sample is readily accessible as for example for pH maasurements (such as by inserting a pH electrode to be thereinto, and/or for sucking out portions such as by means of a syringe and so on, and wherein the blood sample is so accommodated and protected that condensation or evaporation of the blood cannot occur. Other advantages of the invention will be made clearly apparent to those skilled in the art as this description proceeds.

In its broadest aspect, the new equilibrator of the invention comprises an upwardly open vessel or cuvette for blood sample accommodation up to a level below the upper edge of the cuvette. This cuvette is supported for rotation about a vertical axis and is drivedly connected to motor means adapted for controlledly and selectively rotating such cuvette about the vertical axis for promoting centrifugation of the blood sample within the cuvette. A downwardly extended gas outflow passage is arranged within the cuvette and has its lower inlet end at a level well below said upper edge but spaced from the bottom wall of the cuvette.

The equilibrator comprises further an upwardly open gas humidifier vessel designed for accommodating a suitable amount of a proper humidifying liquid at a level not above that defined by the said upper edge of the cuvette. Still further, the equilibrator comprises a stationary container confining therein a thermostatically controlled environment wherein both said rotatable cuvette and said humidifier vessel are accommodated, and including removable cover means for facilitating removal an replacing of the cuvette, the said confined environment including a space above the level defined by the said upper edge of the cuvette. Further, the equilibrator comprises duct means arranged for supplying a gaseous current at the bottom of the said humidifier vessel so that the gas is caused to bubble up through the humidifying liquid to the said space and then to pass over the said upper edge of the cuvette into the cuvette, to pass over the surface and to find its way out of said blood sample, through said outflow passage.

According to a preferred arrangement of the above essential components of the new equilibrator, the said rotatable cuvette, outflow passage, humidifier vessel and container cover are all co-axially arranged about the axis of rotation of the said cuvette. According to a most preferred arrangement, all above components are of cylindrical cross-sectional configuration and have their centers on the said axis so that the most uniform passage of and distribution of the contact area between the gaseous flow and the blood are ensured. According to a further preferred arrangement, the said removable cover consists of a hollow body and has inlet and outlet passages secured thereto for circulation of thermostatically controlled liquid within the hollow of said body. According to another feature of the invention the confined environment within the stationary casing is at least partially flooded with a thermostatically controlled liquid also.

These and other important objects, features and advantages of the invention will be further apparent from the following detailed description of the invention, taken together with the accompanying drawings, forming an essential component of this disclosure.

Figure 2:
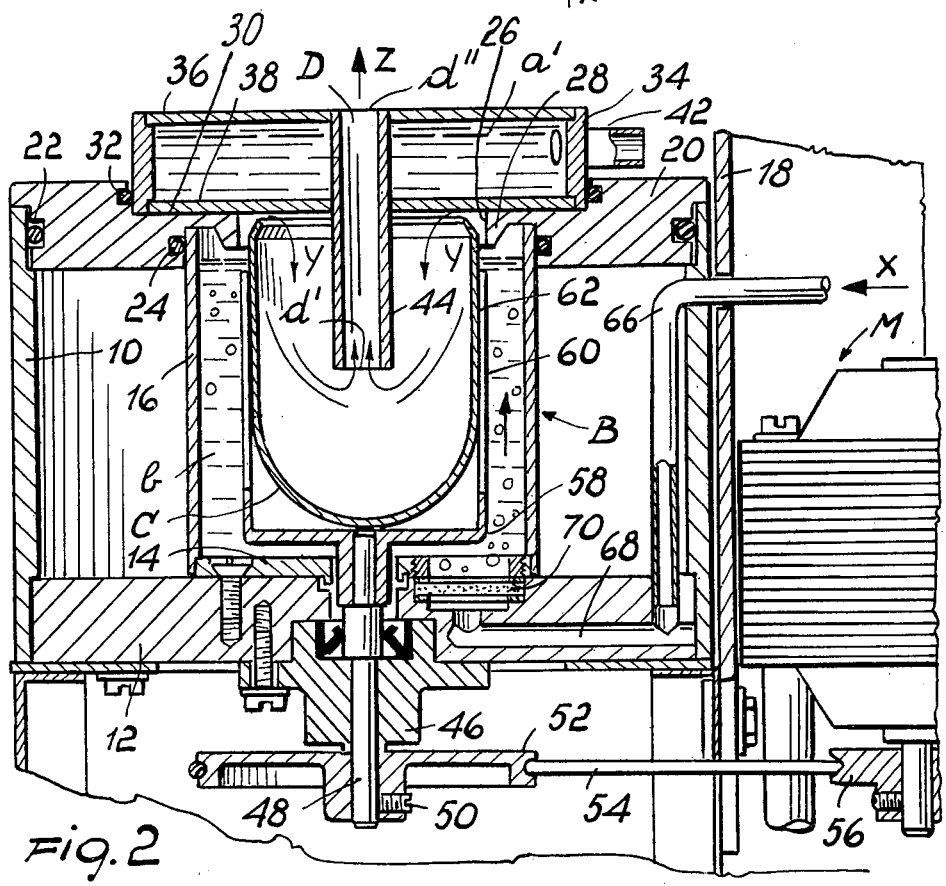

FIG. 1 is a diagramamtical, vertical, cross-sectional view of a first embodiment of the improved equilibrator of the invention;

FIG. 2 is a detailed, cross-sectional, vertical view of a preferred embodiment of the invention, wherein certain structural components and motor and transmission means have been fragmentarily shown as they do not form part of the invention, as individually considered; and FIG. 3 is an exploded view of the essential components of the equilibrator of FIG. 2, the said components being shown partly in cross-sectional view and partly in side elevation.

DESCRIPTION OF PARTICULAR EMBODIMENTS

The general combination of components and parts of the equilibrator, yielding the advantages of the invention, is diagrammatically indicated in FIG. 1. Referring firstly to said figure, the new equilibrator comprises a casing generally indicated at A, having a two-walled cover portion A' and confining therein a closed environment wherein both a humdifier vessel B and a rotatable cuvette C are accommodated. Both said vessel B and cuvette C are upwardly open and adapted to contain a proper amount of humidifying liquid $b$ and a blood sample, respectively, up to levels which are well below the horizontal planes defined by the upper edges of said upwardly open vessels B and C, respectively. Within the said casing A a proper amount of thermostatically controlled liquid $a$ can be caused to circulate, and similarly a thermostatically controlled liquid $a'$ is caused to circulate within the hollow provided in the two-walled cover portion A' of the casing A. The means for circulating the liquids $a$ and $a'$ for thermostatic control of the temperature thereof and for exchanging heat to maintain the desired temperature are not shown, as such means pertain to known art if individually considered.

The said cuvette C has a vertical outflow passage D downwardly projecting thereinto and upwardly extended through the cover portion A'. Such passage has a lower inlet end $d'$ at a level well below the upper edge of the cuvette and possibly well below the level of the blood sample, and an outlet end $d''$ open to the external air. Therefore, a probe, a syringe needle or the like can be inserted through said passage to reach the blood sample for control and measurement purposes. Further, the space confined within the casing A has an unoccupied portion at least above the upper edges of said cuvette C and vessel B, said space being formed, for example, by maintaining the level of the heat carrier liquid $a$ well below said upper edges.

Suitable duct means, connected to a source (not shown) of the desired gas or gaseous mixture, is provided with its outlet portion at the bottom of the humidifier vessel B. Therefore, by supplying such gas or mixture as indicated by arrow X, the gas is caused to upwardly bubble through the humidifying liquid $b$ and reach the unoccupied space thereabove and then, as indicated by arrows Y, pass over the edge of the cuvette C, flow down within the cuvette and into the inlet end $d'$ of the outflow passage D to find its way out as indicated by arrow Z; the passage of the previously humidified gaseous flow within the cuvette C occurring in the presence of and in contacting relationship with the blood sample. The said cuvette C has a vertical axis, is supported within casing A for rotation about such axis, and is drivedly connected to a suitable motor M. This motor is connected to a suitable supply S of electrical current, through a timer device T adapted for adjusting and selectively programming the duration of the rotation and various seuqences of spaced rotation steps. Such motor M and timer T means will not be described in detail as individually they pertain to the well known art of selective actuation of rotary components.

FIGS. 2 and 3 illustrate in detail a preferred embodiment of the invention; wherein the principal components, generally considered as equivalents of those diagrammatically illustrated in FIG. 1, are indicated by the same reference letters, the specific preferred structural details and parts being on the contrary indicated by reference numerals.

In such preferred embodiment, the casing A consists of a generally cylindrical body 10 having a bottom wall 12 fixedly secured thereto. Secured to and above said bottom wall 12 is a minor bottom wall 14 to which is secured a minor cylindrical body 16, which forms the humidifier vessel B. The annular space defined between the said cylindrical bodies 10 and 16 can be used for circulating the heat carrier liquid such as indicated at $a$ in FIG. 1.

The structural stationary assembly comprising the said components 10 and 16 inclusive can be secured to one wall 18 of another casing in which the drive, supply and control components are accommodated.

An outer cover 20 is provided for covering the said annular space between the cylindrical walls 10 and 16, and sealing resilient rings such as indicated at 22 and 24 are provided for fluid-tight engagement with said walls.

Such outer cover 20 has a central opening 26 provided with a downwardly projecting rib 28 thereabout, and has also a shallow seat 30 at its upper face, adapted for fluid-tightly seating a co-axial and disk-like inner and removable cover (embodying the above considered cover A'); the seal being ensured by resilient ring 32 in sealing engagement with the outer surface of the cylindrical side wall 34 of the inner cover A'. Such cover A' comprises an upper wall 36 and a lower wall 38 defining therebetween a space 40 for adapted for circulating the said thermostatically controlled heat carrier $a$. Suitable inlet and outlet passages 42 are provided for circulating such fluid $a'$. The said outflow passage consists of a tubular element 44 fixedly secured coaxially to said inner cover, traversing both its horizontal walls 36 and 38 and downwardly projecting therefrom.

A bushing 46 is fixedly and co-axially secured to said bottom component 12 for rotatably supporting a vertical shaft 48 through such bottom. To the lower end portion of such shaft, external to casing A, the hub 50 of a driven pulley 52 is secured, which is drivedly connected by a belt 54 for example, to a driving pulley 56 (FIG. 2), connected in turn to the output shaft of a fractional motor M, controlledly and selectively fed as above briefly discussed. The upper end portion of shaft 48 is secured to a hub integrally formed in the bottom of a cup-shaped cuvette carrier 60, wherein to the cuvette, generally indicated at C, can be romovably fitted from above. Such cuvette consists of a small cup-shaped vessel 62, preferably but not critically having a hemispherical bottom and an inwardly tapered upper edge portion 64.

The outer diameter of the cuvette is smaller than the inner diameter of said central opening 26 (FIG. 3) of the outer cover 20. As clearly shown in FIG. 2, the above described parts are dimensioned and arranged in the completely assembled device so that a relatively narrow but uninterrupted passage exists within the circular rib 28, outside and above the said edge portion 64 of the cuvette. Therefore, the gaseous flow after bubbling up in the liquid $b$ can pass over the upper edge 64 of the cuvette and then downwardly flow as indicated at Y in FIG. 2 inside the cuvette in presence of the blood sample accommodated thereinto and find its way out at the lower inlet d' of the tubular duct 44 which embodies the outflow passage D.

The gaseous flow can be meteredly supplied at X through duct 66 into a passage 68 bored within the bottom 12 of the casing A and then into the bottom of the inner co-axial vessel B.

Preferably, at the outlet of such duct means a porous diaphragm 70 is provided both for filtering purpose and to provide a means substantially pervious to gases and not pervious to liquids.

By the arrangement described with reference to FIGS. 2 and 3, the operation and maintenance of the device is greatly facilitated. The cuvette C, which can advantageously consist of a cup-shaped body of properly chemically inert material, such as stainless steel, or preferably plastic, such as polyethylene or polypropylene, can be easily removed and replaced upon removal of the inner cover A' and outflow passage D (components 34 to 44 inclusive). The device can be correlated with a suitable number of cuvettes so that time-consuming cleaning and sterilizing operations between different procedures can be avoided by simple substitution of the cuvette. Removal of outer cover 20 facilitates full inspection and cleaning of the inside of the humidifier vessel.

Apart from the advantages resulting from the structure of the device as above described an unexpected and sharp improvement in studying the properties of blood has been found to be attainable by using the new device. A few comments will provide a clear indication of the progress in the art provided by the new equilibrator as follows: The rotation of the cuvette ensures a more ample and intimate contact between the gaseous and liquid phases, and therefore enables the prompt and precise equilibration between blood and gas.

Upon properly programming the switching on and off of motor M, the most desirable equilibration of blood sample is ensured. There is no significant red blood cell hemolysis level and the complete equilibration of blood can be attained in a time sharply shorter than heretofore possible (for example, complete equilibration within about eighteen minutes has been experienced, while prior art tonometric techniques required about twice as much time). Upon laboratory testing of the improved device of the invention, the content of hemoglobin in plasma prior to processing has been found (as determined by the standard Drabkin method) to be 0.108%. Such has been found to be of 0.122 g% after twenty minutes equilibration processing at 37°C, thus proving that no hemolysis of clinical significance has been promoted by processing a blood sample using the device of the invention.

Further, the new device greatly facilitates certain measurements which were heretofore very difficult and time-consuming, such as the determination of the oxygen pressure required for hemoglobin or blood saturation up to 50%; the determination of the oxygen dissociation curves of blood or of hemoglobin solutions relative to various gases, such as $O_2$, $CO_2$, CO and others; the determination of the acid-base status of blood; the determination of the distribution of ions and/or of various substances among plasma and blood red corpuscles; the measurement of blood pH upon blood equilibration with various predetermined gaseous mixtures; the equilibration of solutions which contain unstable or labile biological materials with a gaseous phase of known composition; the equilibration of chemical systems with a known gaseous phase, including sucking-out a part of the equilibrated liquid phase without alteration thereof.

The improvement provided by the invention, resulting in promptness, preciseness, and completeness of measurements, as made possible and feasible by the device of the invention is of paramount importance when considering inter alia, the ever increasing interest in the investigation of oxygen dissociation curves in the occurrence of both acute and chronic respiratory diseases, in the measurement of the physiological properties of stored blood, and in blood and hemoglobin research.

While the details of the new equilibrator device have been described with specific reference to one embodiment thereof, it is evident that the invention should not be and is not limited thereto, and that numerous equivalent devices might be devised by those skilled in the art from the teachings of the invention. Further, it is evident that the same device can be combined with and/or complemented by additional devices and means without departing from the spirit and meaning of the invention.

What is claimed is:

1. A device for providing equilibration of a blood or other liquid sample with a gaseous phase by causing passage of a gaseous stream in presence of said sample, comprising a casing,
    an upwardly open cuvette in said casing for receiving the liquid to be equilibrated, said cuvette having a vertical axis, and an annular upper edge,
    means for supporting said cuvette in said casing for rotation about said vertical axis,
    drive means for rotating said cuvette,
    control means connected to said drive means for providing a sequence of spaced rotation steps to produce intermittent rotation of said cuvette about said vertical axis,
    an outflow passage extending downwardly into said cuvette and having an inlet end below the upper edge of said cuvette,
    and means for supplying a gaseous stream for flow over the upper edge of said cuvette and down into said cuvette for equilibrating contact with liquid in said cuvette as said liquid is being subjected to periodic centrifugating action by said drive means and said control means to cause periodic upward flow of said liquid along the wall of said cuvette, said gaseous stream flowing from said cuvette upwardly through said outflow passage.

2. The device of claim 1 wherein said means for supporting said cuvette is a carrier, said cuvette is a cup-shaped vessel removably secured in said carrier and said drive means comprise a motor drivingly connected to said cuvette carrier and said control means includes means for causing intermittent rotation of said cuvette carrier about said vertical axis by said motor.

3. A device for providing equilibration of a blood or other liquid with a gaseous phase by causing passage of a humidified gaseous stream in presence of said sample, comprising a stationary casing having bottom, side and cover walls and confining therein a space having a lower portion adapted for being flooded by a thermostatically controlled liquid heat carrier and an unoccupied upper portion, an upwardly open vessel in said space, said vessel having its upper edge in said upper portion and adapted for accommodating an amount of humidifying liquid therein at a level below its upper edge, an upwardly open cuvette in said space and having a vertical axis, said cuvette having its upper edge in said upper portion and adapted for accommodating a liquid sample therein at a level below its upper edge, an outflow passage in said casing cover wall, downwardly extending within said cuvette and having an inlet end at a level below the cuvette upper edge, duct means for feeding a gas into said vessel for flow through said humidifying liquid and then into said cuvette over said cuvette upper edge for equilibrating contact with liquid in said cuvette and then from said cuvette upwardly through said outflow passage, means for supporting said cuvette for rotation about said vertical axis, drive means for rotating said cuvette, and a control device connected to said drive means for programming a sequence of spaced rotation steps of said cuvette to subject liquid in said cuvette to periodic centrifugating action and cause periodic upward flow of said liquid along the wall of said cuvette while said liquid is exposed to equilibrating contact with said gas.

4. The device of claim 3 wherein the said drive means comprise a motor drivingly connected to said cuvette and said control device includes timer means for programmedly actuating said motor.

5. The device of claim 3 wherein said vessel has a bottom wall, a port formed in said bottom wall, wherein said duct means has its outlet end in said port, and wherein a diaphragm that is pervious to gases and not pervious to liquids is seated in said port for inflow of said gas at the bottom of said vessel.

6. A device for providing equilibration of a blood or other liquid with a gaseous phase by causing passage of a humidified gaseous stream in the presence of said sample, comprising a stationary casing having bottom, side and cover walls and confining therein a space having an unoccupied upper portion, an upwardly open vessel in said space, said vessel having its upper edge in said portion and adapted for accommodating an amount of humidifying liquid therein at a level below its upper edge, an upwardly open cuvette in said space and having a vertical axis, said cuvette having its upper edge in said portion and adapted for accommodating a liquid sample therein at a level below its upper edge, an outflow passage in said casing cover wall, said passage extending downwardly within said cuvette and having an inlet end at a level below the cuvette upper edge, a removable cover element in said casing cover wall sealingly engaging an opening arranged above said cuvette that is of greater area than the cross-sectional area of said cuvette, said cuvette being removably secured for rotation within said casing and being removable from said casing through said opening, duct means for feeding a gaseous flow at the bottom of said vessel, means for supporting said cuvette for rotation about said vertical axis, and drive means for rotating said cuvette about said vertical axis.

7. The device of claim 6 wherein said outflow passage comprises a vertical duct co-axial to said cuvette and secured to and extending through said removable cover.

8. The device of claim 6 wherein said cuvette support means includes vertical bushing means secured in the casing bottom wall, a vertical shaft rotatably supported in said bushing means and having an upper end within said casing and a lower end outside and beneath said casing, cuvette carrying means secured to said upper end for detachably supporting and rotating said cuvette about said axis, and said drive means is connected to the lower end of said cuvette carrying means.

9. The device of claim 8 wherein said upwardly open vessel has a circular side wall external to and co-axial with said cuvette and defining an annular space for humidifying liquid accommodation about said cuvette up to a level below the upper edge of said cuvette for passage of the humidified gaseous stream from said annular space into said cuvette by passage of the stream above and around its said upper edge, and wherein said casing cover wall comprises an outer cover element having an opening co-axial to and above said cuvette and sealingly engaging both said vessel circular side wall and said casing side wall, and said removable inner cover element has the said outflow passage downwardly extending therefrom and co-axially secured thereto and therethrough and sealingly engaging said opening.

10. A device for providing equilibration of a blood or other liquid with a gaseous phase by causing passage of a humidified gaseous stream in presence of said sample, comprising a stationary casing having bottom, side and cover walls and confining therein a space having an unoccupied upper portion, said casing cover wall having a hollow formed therein, inlet and outlet duct means coupled to said hollow for circulating a thermostatically controlled fluid heat carrier within said hollow, an upwardly open vessel in said space, said vessel having its upper edge in said portion and adapted for accommodating an amount of humidifying liquid therein at a level below its upper edge, an upwardly open cuvette in said space and having a vertical axis, said cuvette having its upper edge in said portion and adapted for accommodating a liquid sample therein at a level below its upper edge, an outflow passage in said casing cover wall, downwardly extending within said cuvette and having an inlet end at a level below the cuvette upper edge, duct means for feeding a gaseous flow at the bottom of said vessel, means for supporting said cuvette for rotation about said vertical axis, drive means for rotating said cuvette, and a control device connected to said drive means for programming a sequence of spaced rotation steps of said cuvette.

11. A device for providing equilibration of a blood or other liquid with a gaseous phase by causing passage of a humidified gaseous stream in presence of said sample, comprising a stationary casing having bottom, side and cover walls and confining therein a space having an unoccupied upper portion, an upwardly open vessel in said space, said vessel having its upper edge in said portion and adapted for accommodating an amount of humidifying liquid therein at a level below its upper edge, duct means for feeding a gaseous flow into said vessel, an upwardly open cuvette in said space, said cuvette having a vertical axis and an inwardly tapered upper edge portion in said portion and adapted for accommodating a liquid sample therein at a level below its upper edge, said casing cover wall comprising an outer cover element having an opening coaxial to and above said cuvette and a downwardly skirting rib about said opening to provide a narrow circular passage about and above the upper edge of said cuvette for passage of a gaseous stream from the space confined within said vessel into said cuvette, an outflow passage extending downwardly from said casing cover wall into said cuvette and having an inlet end at a level below the cuvette upper edge, means for supporting said cuvette for rotation about said vertical axis, and drive means for rotating said cuvette about said vertical axis.

12. A device for providing equilibration of a blood or other liquid sample with a gaseous phase by causing passage of a humidified gaseous stream in presence of said sample, comprising a casing,
  an upwardly open cuvette in said casing for receiving the liquid to be equilibrated, said cuvette having a vertical axis, and an inwardly tapered annular upper edge portion, a downwardly skirting rib to provide a narrow circular passage about and above said cuvette edge for passage of a gaseous stream into said cuvette,
  means for supporting said cuvette in said casing for rotation about said vertical axis,
  drive means for rotating said cuvette about said vertical axis,
  an outflow passage extending downwardly into said cuvette and having an inlet end below the upper edge of said cuvette,
  and duct means for supplying a gaseous stream for flow through said vessel, over the annular upper edge of said cuvette and down into said cuvette for equilibrating contact with liquid in said cuvette as said liquid is being subjected to centrifugating action by said drive means to cause upward flow of said liquid along the wall of said cuvette, said gas flowing from said cuvette upwardly through said outflow passage.

13. The device of claim 12 wherein said casing has a cover wall sealingly engaging an opening above said cuvette support means, said cuvette being removably secured for rotation within said casing and removable through said opening.

14. The device of claim 13 wherein said casing cover wall has a hollow formed therein and inlet and outlet duct means for circulating a thermostatically controlled fluid heat carrier within said hollow.

15. The device of claim 13 and further including a chamber in said casing adapted to be flooded by a thermostatically controlled fluid heat carrier.

16. A device for providing equilibration of a blood or other liquid sample with a gaseous phase by causing passage of a humidified gaseous stream in presence of said sample, comprising a casing,
  an upwardly open cuvette in said casing for receiving the liquid to be equilibrated, said cuvette having a vertical axis and an annular upper edge,
  means for supporting said cuvette in said casing for rotation about said vertical axis,
  drive means for rotating said cuvette about said vertical axis,
  an outflow passage extending downwardly into said cuvette and having an inlet end below the upper edge of said cuvette,
  an upwardly open vessel having a circular side wall external to and co-axial with said cuvette and defining an annular space for humidifying liquid accommodation about said cuvette up to a level below the upper edge of said cuvette for passage of a humidified gaseous stream from said annular space into said cuvette by passage of the stream above and around said upper edge of said cuvette,
  said casing having a cover wall comprising an outer cover element having an opening co-axial to and above said cuvette and sealingly engaging both said vessel circular side wall and the side wall of said casing, a removable inner cover element having said outflow passage coaxially secured thereto and extending downwardly therefrom, through said vessel, over the annular upper edge of said cuvette and down into said cuvette for equilibrating contact with liquid in said cuvette as said liquid is being subjected to centrifugating action by said drive means to cause upward flow of said liquid along the wall of said cuvette, said gas flowing from said cuvette upwardly through said outflow passage.

17. The device of claim 16 wherein said vessel has a bottom wall, a port formed in said bottom wall, and a porous diaphragm seated in said port for inflow of a gaseous stream at the bottom of said vessel, said cuvette support means includes vertical bushing means secured in the bottom wall of said casing, a vertical shaft rotatably supported in said bushing means and having an upper end within said casing and a lower end outside and beneath said casing, cuvette carrying means secured to said upper end for detachably supporting said cuvette, and said drive means is connected to the lower end of said cuvette carrying means, said outflow passage comprises a vertical duct co-axial to said cuvette and secured to and extending through the top of said casing.

18. The device of claim 17 wherein said drive means comprise a motor drivingly connected to said cuvette and means for causing periodic rotation of said cuvette about said vertical axis by said motor.

* * * * *